United States Patent [19]

Crescenzi et al.

[11] Patent Number: 5,384,400
[45] Date of Patent: Jan. 24, 1995

[54] ESTERS OF PECTIC AND PECTINIC ACID

[75] Inventors: Vittorio Crescenzi, Rome; Lanfranco Callegaro, Padova, both of Italy

[73] Assignee: M.U.R.S.T. (Italian Ministry for Universities and Scientific and Technological Research), Rome, Italy

[21] Appl. No.: 3,732

[22] Filed: Jan. 13, 1993

[30] Foreign Application Priority Data

Jan. 13, 1992 [IT] Italy .......................... PD92A000004

[51] Int. Cl.$^6$ .................. C08B 37/06; C13F 3/00; A61K 6/00
[52] U.S. Cl. ........................ 536/2; 424/401; 426/658; 426/659; 426/660; 127/29; 604/358; 604/365; 604/368
[58] Field of Search .................. 536/2; 514/777; 424/401; 604/358, 365, 368; 426/658, 659, 660; 127/29

[56] References Cited

U.S. PATENT DOCUMENTS

| | | | |
|---|---|---|---|
| 2,960,498 | 11/1960 | Nager | 536/2 |
| 3,326,760 | 6/1967 | Halpern et al. | 204/256 |
| 4,461,890 | 7/1984 | Manabe et al. | 536/2 |
| 5,008,254 | 4/1991 | Weibel | 536/2 |
| 5,071,970 | 12/1991 | le Grand et al. | 536/2 |

FOREIGN PATENT DOCUMENTS

| | | |
|---|---|---|
| 49-039192 | 10/1974 | Japan . |
| 50-023671 | 8/1975 | Japan . |
| 63942 | 3/1949 | Netherlands . |
| 584012 | 12/1977 | U.S.S.R. . |

OTHER PUBLICATIONS

Kratchanov et al "Synthesis and properties of ethyl esters of sunflower pectiz acid" Carbohydrate Research, 80(1980) 350–353.
Aimukhamedova et al "Glycerol pectate" Chemical Abstracts vol. 88, 1978, Abstract No. 107095d.

*Primary Examiner*—Nathan M. Nutter
*Attorney, Agent, or Firm*—Birch, Stewart, Kolasch & Birch

[57] ABSTRACT

Pectic acid and pectinic acid may be totally or partially esterified with aliphatic, arylaliphatic, cycloaliphatic or heterocyclic alcohols. When the acid is only partially esterified, the remaining free carboxyl groups may be salified with inorganic or organic bases. The esters may be used in the pharmaceutical, biomedical, alimentary and cosmetic fields. The esters may be prepared from a quaternary ammonium salt of pectic acid or pectinic acid and an esterifying agent such as a halogenide.

20 Claims, No Drawings

ESTERS OF PECTIC AND PECTINIC ACID

OBJECT OF THE INVENTION

The present invention relates to pectic and pectinic acid (hereafter called PGA and PGA-Me-x respectively), totally or partially esterified, salts of partially esterified PGA and PGA-Me-x with metal ions or organic bases, a process for the preparation thereof, pharmaceutical preparations and/or medicaments comprising the total or partial esters of PGA and PGA-Me-x or salts thereof and the use of the total or partial esters or salts thereof in the pharmaceutical, biomedical, alimentary and cosmetic fields.

SUMMARY AND FIELD OF THE INVENTION

In the specification and claims the term "partial ester" is used to designate an acid which is partially esterified, which means that only a certain amount of the available free carboxyl groups of pectic acid or pectinic acid are esterified.

In the specification and claims, wherever the meaning does not clearly exclude this possibility, the term "esters of PGA and PGA-Me-x" should be taken to mean both the esters themselves and their salts, and the term "ester" is used to designate both a total and a partial ester unless otherwise explained.

The invention describes more precisely esters and processes for the preparation of:

natural demethoxylated pectins, pectic acids or polygalacturonic acids (hereinafter known as PGA) wherein all or only part of the carboxyl groups are esterified and the salts of the partial esters with metal ions and with organic bases which are acceptable for pharmacological use or in foodstuffs.

natural pectins, pectinic acids (hereinafter known as PGA-Me-x), that is, PGA's in which a given fraction, x %, of the carboxyl groups of the galacturonic acid residues are naturally in the form of the methyl ester, and wherein the non-methoxylated carboxyl groups are partially or totally esterified with alcohols other than methyl alcohol, and the salts of the partial esters with metal ions or with organic bases which are acceptable for pharmacological use or as foodstuffs.

These new esters possess, according to the nature of their ester groups and to their degree of esterification, interesting rheological, gelling, emulsifying, bioplastic, film-forming properties respectively, and can be used in numerous sectors of industry such as the biomedical, sanitary, agro-alimentary, and cosmetic fields. The invention also includes compositions containing as active ingredient one or more esters of PGA and/or PGA-Me-x or one of their salts as defined above, as well as medicaments containing:

a pharmacologically active substance or an association of pharmacologically active substances and,
a vehicle constituted by a partial or total ester of PGA and/or PGA-Me-x.

BRIEF DESCRIPTION OF THE INVENTION

The present invention relates to new polysaccharide esters and more precisely esters of PGA and PGA-Me-x, as well as processes for their preparation. The invention also includes the use of said esters of PGA and PGA-Me-x, as well as manufactured products based on the same esters, in various sectors of industry, especially in pharmaceuticals, cosmetics and agriculture. The new esters according to the invention include total esters and partial esters of PGA. In the partial esters the non-esterified carboxyl groups may be salified with metal ions from inorganic bases or with organic bases, and such salts, like the industrial articles which contain them, form part of the invention.

The new esters also include products made with PGA-Me-x in which the free fraction of the carboxyl groups is partly or completely esterified with alcohols other than methyl alcohol: in the case of partial esters the residual free carboxyl groups may be salified with metal ions or organic bases, and such salts, like the industrial articles which contain them, also form part of the invention.

Specifically, the esters according to the invention are pectic and pectinic acids totally or partially esterified in which the esterifying component is derived from aliphatic, arylaliphatic, cycloaliphatic and heterocyclic alcohols, salts of such partially esterified pectic and pectinic acids with inorganic or organic bases.

TECHNOLOGICAL BACKGROUND

PGA's are polysaccharides, commonly present in plants, relatively heterogeneous from a structural point of view and essentially definable as galacturonic glycans (poly (1→4)-α-D-galactopyranosiluronic acids, sometimes called pectic acids.

Apart from residues of α-D-galacturonic acid, very prevalent and present in blocks of 25–30 consecutive units, PGA's contain along their chains some residues of neutral monosaccharides—generally not exceeding about 15%—in particular β-L-rhamnose.

The chains of PGA may also contain branches (for example short arabinogalactan chains) bound (1→4) mainly to the rhamnose residues.

One characteristic of PGA is that it forms gels which are stable in aqueous media in the presence of Ca(II) ions, even in the absence of added sugar. Of equal note are mixed thermoreversible gels prepared from acid aqueous solutions in the absence of Ca(II) ions and sucrose, containing PGA and alginates.

Thanks to the complete biocompatibility of their components, such gels are of particular interest in the fields of foodstuffs, pharmaceuticals and cosmetics.

PGA's also exhibit interesting rheological characteristics in aqueous media. Some PGA-Me-x (x being about 50%) from particular vegetable sources contain acetyl groups (about 2–9% by weight) which may on the one hand attenuate these polymers' gel-forming characteristics but also give them remarkable tensioactive and in particular emulsifying properties (stabilization of oil-in-water emulsions).

PGA-Me-x, widely present in plants, may have substantially identical chains to those of PGA's, while an x % fraction of the residues of galacturonic acid in the chain is in the methyl ester form.

The value of x % depends on the natural source used to extract the biopolymers and normally comes within the range of about 10% to about 75%. Depending on the degree of methylation, expressed as x % Me, the PGA-Me-x's exhibit characteristic gel-forming properties in aqueous media not only in the absence of calcium ions but also for example in the presence of sufficient concentrations of sucrose. It is well known that various PGA-Me-x's are used in the food industry, thanks to these very properties.

Chemical modification methods for pectins are known which are based on demethoxylation to increase solubility of the polymer (U.S. Pat. No. 4,016,351 issued Apr. 5, 1977). In the citation of the chemical possibilities, not all the reactions intervening on the hydroxy and/or dihydroxy groups were considered, but only the carboxyl group was targeted. To date, only the synthesis of pectin partial esters of simple aliphatic alcohols, notably ethanol, has been carried out using PGA-Me-x samples, in particular citrus and sunflower pectic acids, (C. G. Kratchnov et al., Carbohyd. Res., 80, 350 (1980); which refers to Z. I. Kertesz, "The Pectic Substances", Interscience, New York (1951); R. McDonnell et al., Arch. Biochem., 28, 260 (1950); and H. Duel, Ber. Schweiz, Bot. Ges., 53, 219 (1943)). However, the method of synthesis employed (PGA-Me-x in alcoholic mineral acids) leads to severe chain degradation and fails to yield mixed esters because of a concomitant, extensive trans-esterification side-reaction.

DETAILED DESCRIPTION OF THE INVENTION

By altering the charge density and the hydrophilic character of the PGA and PGA-Me-x chains by partial esterification of the free carboxyl groups, it is possible to drastically alter the properties of the resulting polyester(s) both in terms of solubility and behavior in solution and in terms of gel- and/or film-forming and/or emulsifying properties.

Indeed, it is possible to introduce by esterification into the chains of PGA and PGA-Me-x hydrophobic or hydrophilic functions thereby strongly influencing—in a controlled manner—the propensity of the ester derivative to mix with organic solvents or aqueous media, as well as the characteristics of the mixtures themselves.

One group of esters according to the invention are esters of pectic and pectinic acids wherein the alcohol component is derived from aliphatic alcohols with up to 34 carbon atoms which may be saturated or unsaturated, said alcohols being unsubstituted or substituted by one or more, especially two functional units selected from the group consisting of amino, hydroxy, mercapto, aldehydo, keto, carboxyl, hydrocarbyl- and dihydrocarbylamino, ether, ester, thioether, thioester, acetal, ketal, carbalkoxy, carbamide and carbamide groups substituted by one or two hydrocarbyl groups, and in which such aliphatic alcohols may be interrupted in the carbon atom chain by heteroatoms chosen from the group formed by oxygen, sulphur and nitrogen, and salts thereof.

A subgroup of the above-mentioned esters is formed by esters of pectic and pectinic acids and salts thereof, in which the esterifying alcohol component is derived from an alcohol with a maximum of 12 carbon atoms and in the case of alcohols substituted by functional units, the hydrocarbyl radicals of the amino, ether, ester, thioether, thioester, acetal, and ketal groups are $C_1$-$C_4$ alkyl groups and the hydrocarbyl groups in the substituting esterified carboxyl groups and in the substituted carbamide groups are $C_1$-$C_4$ alkyl groups, and wherein the substituted amino or carbamide groups may also be alkylene amino or alkylene carbamide groups with a maximum of 8 carbon atoms.

Specific esters of the above-mentioned subgroup of esters are esters in which the esterifying alcohol component is derived from ethyl, propyl, isopropyl, n-butyl, isobutyl, tert-butyl, amyl, pentyl, hexyl, octyl, nonyl, decyl or dodecyl alcohol.

Of the substituted alcohols the bivalent alcohols should be listed, such as ethylene glycol, propylene glycol or butylene glycol, the trivalent alcohols such as glycerine, aldehydo alcohols such as tartronic alcohol, carboxyl alcohols such as lactic acids, for example α-oxypropionic acid, glycolic acid, malic acid, tartaric acids, citric acid, aminoalcohols, such as aminoethanol, aminopropanol, n-aminobutanol and their dimethyl and diethyl derivatives in the amine function, choline, pyrrolidinylethanol, piperidinylethanol, piperazinylethanol and the corresponding derivatives of n-propyl or n-butyl alcohols, monothioethylene glycol or its alkyl derivatives, for example the ethyl derivative in the mercapto function.

Of the higher saturated aliphatic alcohols, those worthy of special mention are for example cetyl alcohol and myristyl alcohol, but especially important for the purposes of the present invention are higher unsaturated alcohols with one or two double bonds, such as especially those contained in many essential oils and having an affinity with terpenes such as citronellol, geraniol, nerol, nerolidol, linalool, farnesol, and phytol.

Of the lower unsaturated alcohols consideration should be given to propargyl alcohol.

Specific mention should be made of glycerine esters of pectic and pectinic acids and salts thereof.

A second group of esters according to the invention are esters of pectic and pectinic acids wherein the alcohol component is derived from arylaliphatic alcohols with only one benzene residue and wherein the aliphatic chain has a maximum of 4 carbon atoms and wherein the benzene residue may be substituted by 1 to 3 substituents selected from the group consisting of methyl, hydroxy and halogen, especially chlorine, bromine or iodine, and wherein the aliphatic chain may be substituted by one or two units selected from the group consisting of free amino groups, mono- or diethylated amino groups, pyrrolidine and piperidine groups, and salts thereof.

A subgroup of the above-mentioned esters is formed by esters of pectic and pectinic acids in which the esterifying alcohol component is derived from benzyl alcohol, phenethyl alcohol, ephedrine or adrenaline.

A third group of esters according to the invention are esters of pectic and pectinic acids wherein the alcohol component is derived from cycloaliphatic, aliphatic-cycloaliphatic or heterocyclic alcohols with a maximum of 34 carbon atoms. The cyclic alcohols can be mono- or polycyclic. Among monocyclic alcohols special mention should be given to those with a maximum of 12 carbon atoms, with rings containing preferably between 5 and 7 carbon atoms, possibly substituted for example by between one and three lower alkyl groups, such as methyl, ethyl, propyl or isopropyl groups. Specific alcohols of this group are cyclohexanol, cyclohexanediol, 1,2,3cyclohexanetriol and 1,3,5 cyclohexanetriol (phloroglucitol), inositol, the alcohols derived from p-menthane such as carvomenthol, menthol, α and γ-terpineol, 1-terpineol, 4-terpineol and piperitol, or a mixture of these alcohols known as "terpineol", 1,4- and 1,8-terpin. A preferred cycloaliphatic alcohol is cyclohexylalcohol. Polycyclic aliphatic cycloaliphatic alcohols for use in obtaining the esters of the present invention are sterols, cholic acids and steroids, such as sexual hormones and the synthetic analogues, in particular corticosteroids and their derivatives. Thus for example it is possible to use: cholesterol, dihydrocholesterol, epidihydrocholesterol, coprostanol, epicoprostanol, sitosterol, stigmasterol, ergosterol, cholic acid, deoxycholic acid, lithocholic acid, estriol, estradiol, equilenin, equilin and their alkyl derivatives, as well as their ethynyl or propynyl derivatives in position 17, for example 17-α-ethynyl-estradiol or 7-α-methyl-17-α-ethynylestradiol, pregnenolone, pregnanediol, testosterone and its derivatives, such as 17-α-methyltestosterone, 1,2-dehydrotestosterone and 17-α-methyl-1,2-dehydrotestosterone, the alkyl derivatives in position 17 of testosterone and of 1,2-dehydrotestosterone, such as 17-α-ethynyltestosterone, 17-α-propynyltestosterone, norgestrel, hydroxyprogesterone, corticosterone, deoxycorticosterone, 19-nortestosterone, 19-nor-17-α-methyltestosterone and 19-nor-17-α-ethynyltestosterone, cortisone, hydrocortisone, prednisone, prednisolone, 6-α-methyl prednisolone, fludrocortisone, dexamethasone, betamethasone, paramethasone, flumethasone, fluocinolone, fluprednylidene, clobetasol, beclomethasone, aldosterone, deoxycorticosterone, alphaxolone, alphadolone, bolasterone and anti-hormones such as cyproteroneo Other alcohols to be used according to the invention are alcohols which are vitamins, such as axerophthol, vitamins $D_2$ and $D_3$, aneurine, lactoflavine, ascorbic acid, riboflavine, thiamine and pantothenic acid. As examples of heterocyclic alcohols may be mentioned furfuryl alcohol, alkaloids and their derivatives such as atropine, scopolamine, cinchonine, cinchonidine, quinine, morphine, codeine, nalorphine, N-butylscopolammonium bromide, ajmaline; phenylethylamines such as ephedrine, isoproterenol, epinephrine; phenothiazine drugs such as perphenazine, pipotiazine, carphenazine, homofenazine, acetophenazine, fluphenazine, N-hydroxyethylpromethazine chloride; thioxanthene, drugs such as flupenthixol, clopenthixol; anticonvulsants such as meprophendiol, antipsychotic drugs such as opipramol; antiemetics such as oxypendyl; analgesics such as carbetidine, phenoperidine and methadol; hypnotics such as etodroxizine; anorexics such as benzhydrol and diphemethoxidine; minor tranquilizers such as hydroxyzine; muscle relaxants such as cinnamedrine, diphylline, mephenesin, methocarbamol, chlorphenesin, 2,2-diethyl-1,3-propanediol quaifenesin and idrocilamide; coronary vasodilatators such as dipyridamole and oxyfedrine; adrenergic blockers such as propanolol, timolol, pindolol, bupranolol, atenolol, metoprolol, practolol; antineoplastics such as 6-azauridine, cytarabine, floxuridine; antibiotics such as chloramphenicol, thiamphenicol, erythromicin, oleandomycin, lincomycin; antivirals such as idoxuridine; peripheral vasodilators such as isonicotinyl alcohol; carbonic anhydrase inhibitors such as sulocarbilate; anti-asthmatics and anti-inflammatories such as tiaramide; and sulfamidics such as 2-p-sulfanylanilinoethanol.

When the pectic acid or pectinic acid is not totally esterified, it is preferred that the degree of esterification is between 5% and 95%, preferably between 10 and 85%, more preferably between 15 and 75%.

The degree of esterification is to be adapted according to the final use of the esterified pectic or pectinic acid.

In one aspect of the invention, all carboxyl groups of pectic acid or pectinic acid are esterified.

When the pectic acid or pectinic acid is only partially esterified, the remaining free carboxyl groups may be salified. Salifying ions can be selected from the group consisting of metal ions, alkaline metal ions, alkaline metal ions, and ammonium ions. Salts may also be prepared with organic bases.

The salifying metal ions can be selected from the group consisting of alkaline metal ions such as sodium and potassium ions, alkaline earth metal ions such as calcium and magnesium ions. The salifying organic bases can be selected from the group consisting of amino bases, specifically aliphatic, arylaliphatic, cycloaliphatic or heterocyclic amines, and the salifying amino bases are preferably therapeutically acceptable.

It is important that the chemical esterification procedure should allow not only good yields of products with easily controllable degrees of esterification of the mixed esters, if desired, but also to keep the chain length as intact as possible. In contrast to the known methods for chemical modification of pectins which degrade the polymer, i.e. cause a decrease in chain length and, hence, in molecular weight, the process according to the invention does only cause a slight decrease, if any, in the chain length of the polymer.

The methods reported in the literature, moreover, do not allow the controlled obtainment of mixed esters, that is, esters in which the ratio between different ester residues can be quantitatively fixed, (e.g. from 0.1 to 0.9).

A simple procedure has now been discovered, within the scope of the present invention, convenient to use and free from degrading effects, for the preparation of esters of PGA and PGA-Me-x, wherein quaternary ammonium salts of PGA and PGA-Me-x are reacted with conventional esterifying agents in organic solvents, preferably aprotic solvents. This process offers a large number of new esters of PGA and PGA-Me-x, especially the esters of monovalent, aliphatic, arylaliphatic, alicyclic and heterocyclic alcohols.

According to the chemically new and original process of the present invention, the esters of PGA and PGA-Me-x can advantageously be prepared with good yields starting from quaternary ammonium salts of PGA and PGA Me-x, preferably lower tetraalkylammonium salts, especially tetrabutylammonium salts, by reaction with an esterifying agent in suitable organic solvents such as N-methyl-pyrrolidone, dialkylsulfoxides, in particular lower alkyl dialkylsulfoxides and above all dimethylsulfoxide. Other solvents, not always aprotic, should also be considered, such as alcohols, esters, ester ketones, especially alcohols and aliphatic or heterocyclic ketones with low boiling points, such as hexafluoroisopropanol and trifluoroethanol.

The reaction should be performed preferably at temperatures of between about 0° C. and 100° C. and especially between about 25° C. and 75° C., for example at about 30° C.

Esterification is performed preferably by gradually adding the esterifying agent to said ammonium salt dissolved in one of the above-mentioned solvents, for example in dimethylsulfoxide.

It is possible to use, as esterifying agents, alkylating agents such as alkyl or arylalkyl halogenides.

The quaternary ammonium salts of PGA or PGA-Me-x can be prepared by reacting the sodium salt of PGA or PGA-Me-x in an aqueous solution with a resin salified with a quaternary ammonium base (e.g., tetrabutylammonium ions). As starting material, it is convenient to use the sodium salt of PGA or PGA-Me-x, because the sodium salts are the prevalent form of these natural products, easily available commercially. After equilibration, the tetrabutylammonium salt of PGA or PGA-Me-x can be recovered by elution, followed by optional filtration and freeze-drying.

These salts are easily soluble in the above-mentioned organic solvents. Before they are subjected to the subsequent esterification reaction, it is necessary to eliminate any water or oxygen from the reaction system. This elimination may be performed by bubbling dry, inert gas through the solution. As a drying gas, nitrogen may be used. Oxygen will be removed by this procedure together with any water. As an extra precaution it is possible to use e.g. an anisole derivative such as e.g. 3-tert-butyl-4-hydroxy anisole as a free radical inhibitor. Thereafter, the esterification can be performed by gradually adding an alkylating agent of the type specified above. In this manner, esterification is achieved in a homogeneous phase, and the percentage of carboxyl groups of PGA or PGA-Me-x to be esterified can be regulated as desired.

To obtain mixed esters of PGA, in which two or more given fractions of carboxyl groups are esterified with different alkyl (or arylalkyl) residues, it is sufficient to use in the above described reaction the two or more corresponding alkyl (or arylalkyl) halogenides either together or one after the other.

It is especially preferred to prepare esters of pectic acid and pectinic acid in which there are two esterifying groups. When this is the case, the molar ratio between the two esterifying groups varies between 0.1:1 and 1:0.1. It is especially preferred to prepare mixed esters in which the molar ratio between the esterifying groups is between 0.2:1 and 1:0.2, preferably at about 1:1. This applies to both partially and totally esterified pectic and pectinic acid. If the overall degree of esterification is e.g. 60%, and the ratio between two esterifying alcohol groups is 0.5:1 it means that the first alcohol esterifies 20% of the carboxyl groups and the second alcohol esterifies 40% of the carboxyl groups.

A variation of the above-described process consists in reacting a metal salt such as a sodium or potassium salt of PGA or PGA-Me-x, suspended in a suitable solvent, such as dimethylsulfoxide, with an appropriate alkylating agent in the presence of catalytic quantities of a quaternary ammonium salt, in particular tetrabutylammonium iodide.

In yet another variant, a salt of PGA (e.g. the sodium salt) or a salt of PGA-Me-x (e.g. the sodium salt) is transformed into acid form by ion exchange on a sulfonic resin in acid form. The free acid form of PGA is then neutralized with aqueous tetrabutylammonium hydroxide.

In all cases, after a sufficiently long reaction time (between one and three days) the ester derivative of PGA or PGA-Me-x is recovered from the reaction mixture by cold precipitation in a non-solvent such as ethyl acetate or acetone.

The derivative is then washed repeatedly with non-solvent(s) and then vacuum-dried, e.g. at about 50° C.

In particular, depending on the nature of the esterifying groups, the partial esters of PGA are easily soluble in water. When this is the case, the derivative can be further purified by dissolution in concentrated aqueous NaCl, whereby the free carboxyl groups are salified with sodium ions, and subsequently, by repeated dialysis against distilled water. The partial ester of PGA-sodium salt can be isolated by freeze-drying. Partial esters of PGA not soluble in water can be solubilized in organic solvents, e.g. dimethylsulfoxide. This is also the case of the total esters.

The new esters of PGA and PGA-Me-x can be used in the pharmaceutical, sanitary, cosmetic, and alimentary fields.

Consequently, a further aspect of the invention relates to a method for using the new esters and salts thereof and industrial articles and products prepared with the esters or salts thereof, such as cosmetic, sanitary, pharmaceutical or alimentary articles, and especially emulsifying and thickening agents.

If the esterifying component is derived from a pharmacologically active alcohol, or if the salt-forming organic base is a pharmacologically active compound, the ester of pectic acid or pectinic acid and the salts thereof can be used as an active ingredient in pharmaceutical compositions. As pharmacologically active salt-forming organic bases can be mentioned azotized and basic drugs such as those included in the following groups: alkaloids, peptides, phenothiazine, benzodiazepine, thioxanthenes, hormones, vitamins, anticonvulsants, antipsychotics, antiemetics, anesthetics, hypnotics, anorexics, tranquilizers, muscle relaxants, coronary vasodilators, antineoplastics, antibiotics, antibacterials, antivirals, antimalarials, carbonic anhydrase inhibitors, nonsteroid anti-inflammatories, vasoconstrictors, cholinergic agonists, cholinergic antagonists, adrenergic agonists, adrenergic antagonists, and narcotic antagonists.

Accordingly, another aspect of the invention relates to pharmaceutical compositions which contain, as the active ingredient, an ester of pectic or pectinic acid with a pharmacologically active alcohol or a salt of an ester of pectic or pectinic acid, said salt being derived from a pharmaceutically active organic base.

An interesting group of esters for use in therapy is represented by the esters in which the pharmacological qualities of the alcohol component are dominant, that is, pectic and pectinic acid esters with pharmacologically active alcohols, such as steroidal alcohols, such as those of the cortisone type. These esters possess properties which are qualitatively similar to those of the alcohol, but with a wider range of action. Even as compared to already known esters of such pharmaceutically active alcohols the novel esters according to the invention ensure a more balanced, constant and regular pharmacological action and generally cause a marked retard effect of the active alcohol component.

Still another interesting group of esters according to the present invention, and representing a particularly original and useful aspect of the same, is that of the esters of a more mixed character compared to the above-mentioned. That is, esters in which one part of the carboxylic groups of pectic or pectinic acid are esterified with a pharmacologically active alcohol and another part with a pharmacologically inactive alcohol, or the activity of which is negligible. By suitably dosing the percentages of the two types of alcohol as the esterifying component, it is possible to obtain esters with the same activity as the pharmacologically active alcohol and having those qualities mentioned above of increased stability and bioavailability compared to the desired and characteristic activity of the pharmacologically active alcohol and due to the ester groups of the pharmacologically inert acid.

Still another group of esters is represented by those of a mixed character in which the ester groups derive from two different therapeutically active substances. In this case also, the esters may be partial or total, that is, only some carboxylic groups derive from two different therapeutically active alcohols, for example from a cortisone steroid and from an antibiotic, while the other groups may be free or salified, for example with alkaline metals, above all sodium, or all the carboxylic groups are esterified with the above mentioned alcohols. It is possible, however, to prepare esters with three or more alcohol components, for example esters in which a part of the carboxylic groups are esterified with a therapeutically active alcohol, another part with another therapeutically active alcohol, a third part with a therapeutically inactive alcohol and a fourth part is possibly salified with a metal or with a therapeutically active or inactive base, or it is in a free form. Furthermore, the invention relates to pharmaceutical compositions which contain, as the active ingredient, pectic or pectinic acid partially esterified with a bivalent aliphatic, pharmacologically active alcohol.

Further to the active ingredient, such pharmaceutical compositions may comprise an excipient, which is suitable for enteral or parenteral application. The active ingredient may e.g. be formulated with the usual carriers for tablets, pellets, capsules, suppositories, solutions, emulsions, aqueous suspensions, inhalatives, and other suitable administration forms.

Examples of carriers are glucose, lactose, gum acacia, gelatin, mannitol, starch, magnesium silicate, talc, and other carriers suitable for use in manufacturing compositions in solid, semisolid, or liquid form or in microencapsulated form, and in addition, auxiliary, stabilizing, thickening, coloring, flavoring and preservative agents can be incorporated in the compositions of the invention.

The active ester or a salt thereof, which also may be an active component, is included in the compositions of the invention in an amount sufficient to produce the desired therapeutical effect upon administration. The dosage or therapeutically effective quantity of the active ester and/or the active salt thereof varies and also depends upon the age and condition of each individual patient being treated.

The pharmaceutical compositions according to the invention can be formulated for administration in any convenient way and adapted for parenteral administration, subcutaneous administration, intradermal administration or local or topical administration such as oral, rectal, vaginal or nasal administration.

The esters of PGA and PGA-Me-x according to the present invention can also be utilized in the formulation of vehicles for pharmacologically active substances for humans or animals (substances with a topical, oral or rectal action) or for substances with specific biological activity on plants (e.g. herbicides).

The present invention relates to the above-mentioned new use of esters of PGA and PGA-Me-x and salts thereof and products prepared with these esters, especially compositions containing an ester of PGA or PGA-Me-x or a salt thereof as vehicle for biologically active substances.

In particular, in formulations designed to serve as vehicles for one or more biologically active substances, this result can be achieved by utilizing basic, pharmacologically active substances used to salify part or all of the free carboxyl groups of partial esters of PGA and PGA-Me-x.

The present invention provides an assortment of new substances with more advantageous effects for special products to be used in cosmetics, sanitary articles, pharmaceuticals, alimentary articles, and in fields in which their thickening and/or emulsifying properties can be utilized. These effects vary of course from case to case, according to the use of the product.

It is important to point out the superiority of the esters of monovalent alcohols according to the present invention since monovalent alcohol residues are metabolized in the organism to degradation products which are less toxic than glycols. An important exception in the context is represented by biocompatible glycols (e.g. oligo-ethyleneglycols) or polyhydroxylated species (e.g. glycerol and sugars).

An especially preferred sub-group of esters are esters derived from alcohols which do not contain toxic substituents, especially aliphatic or cycloaliphatic monovalent alcohols.

Esters with aliphatic or cycloaliphatic monovalent alcohols are, therefore, of great advantage especially in the food industry for the above-mentioned uses.

The very low toxicity of the esters of numerous monovalent alcohols of PGA and PGA-Me-x according to the present invention can advantageously be utilized mainly in the pharmaceutical, cosmetic, sanitary, and agricultural and alimentary fields, where the new esters of PGA and PGA-Me-x can be used as biocompatible plastic materials with various functions.

Thus, for example, the esters of PGA and/or PGA-Me-x can be used as additives for a wide variety of polymeric materials used for sanitary articles, as starch and derivatives thereof, cellulose and derivatives thereof, polyurethanes, polyesters, polyamides, polysiloxanes, some vinyl and acrylic polymers, with the effect of increasing the biocompatibility of the resulting polymeric mixtures.

In the cosmetic and pharmaceutical fields the esters of PGA and/or PGA-Me-x of the invention can be used to prepare ointments, creams and other types of medicaments for topical application or cosmetic products, such as sunshield creams, where they can act as stabilizers or emulsifiers.

In the pharmaceutical field, the esters of PGA and/or PGA-Me-x and salts thereof can be used as disintegrants for tablets or as binding agents, but above all, according to a particularly important aspect of the present invention, they can be used as vehicles for pharmacologically active substances.

The new esters of PGA and PGA-Me-x or salts thereof can act as vehicles for other substances in various ways, and in particular (but not only):
  the esters of PGA or PGA-Me-x or salts thereof act as vehicle in the full sense of the word, e.g. as carriers or as pro-drugs, and are associated chemically or physically to the active substance (for example in the form of microspheres);
  the partial ester of PGA or PGA-Me-x is salified with the active substance.

The main object of the present invention is therefore represented by the total or partial esters of PGA and PGA-Me-x with alcohols of the aliphatic, arylaliphatic, cycloaliphatic or heterocyclic series and salts of the partial esters with inorganic or organic bases.

A second object of the invention is represented by the procedure for the preparation of esters of PGA and PGA-Me-x, characterized by treating a quaternary ammonium salt of PGA with an esterifying agent in an aprotic solvent, and if desired, in salifying in the partial esters of PGA or PGA-Me-x thus obtained the free carboxyl groups with preselected inorganic or organic bases.

A third object of the invention is constituted by the use of esters of PGA or PGA-Me-x as vehicles for substances to be used in the cosmetic field, for pharmacologically active species and for pharmaceutical preparations or medicaments including:
a pharmacologically active substance or an association of pharmacologically active substances;
a carrying vehicle including a total or partial ester of PGA or PGA-Me-x, or partial ester salts of PGA or PGA-Me-x with inorganic or organic bases, possibly also physically combined with other biocompatible polymers.

In this manner, pharmaceutical compositions or medicaments can be constituted by a partial ester of pectic or pectinic acid, possibly salified by inorganic or organic bases, wherein at least a fraction of the carboxyl groups is salified by a therapeutically active base.

The pharmacologically active substance can be selected from the group consisting of analgesics, anesthetics, antiinflammatories, vasoconstrictors, antibiotics, antibacterials, and antivirals.

An interesting aspect of the invention relates to the use of pharmacologically active esters of pectic acid or pectinic acid or salts thereof in the fields of ophthalmology, dermatology, dentistry or neurology.

Cosmetic articles according to the invention contain an ester of pectic acid or pectinic acid or a salt of a partial ester of pectic acid or pectinic acid, optionally together with other ingredients usually used in cosmetic articles such as water, emulsifiers, oils, perfumes or colorants. In the cosmetic articles according to the invention, the ester, whether total or partial, is derived from a therapeutically and pharmacologically inactive alcohol.

Preferred cosmetic articles according to the invention comprise esters derived from aliphatic alcohols with a maximum of 12 carbon atoms.

Another aspect of the invention relates to sanitary or surgical articles containing an ester of pectic or pectinic acid according to the invention and as defined above or containing an ester of pectic or pectinic acid derived from a bivalent aliphatic alcohol.

A preferred embodiment is formed by sanitary or surgical articles as defined above, constituted by films or threads of esters of pectic or pectinic acid or salts thereof in which the esterifying and salifying components both are derived from therapeutically inactive substances. In films or threads of the invention, the alcohols which totally or partially esterify the carboxyl groups in pectic or pectinic acid are aliphatic alcohols with a maximum of 12 carbon atoms. Threads of esters of pectic acid or pectinic acid can be used as suture threads in surgical operations.

Still another aspect of the invention relates to the esters of pectic or pectinic acid or salts thereof, prepared in film, sheet or thread form, to be used in the agricultural-alimentary sector as carriers for biologically active species beneficial to plants and vegetables or as protective wrappings for foods.

Films, sheets or threads according to the invention can be made in a procedure in which the ester of pectic or pectinic acid is dissolved in an organic solvent, the solution is made into a sheet or film, or spun into a thread, and then the organic solvent is eliminated by treatment with a second suitable organic or aqueous solvent, which is soluble in the first solvent. The film, sheet or thread must not be soluble in said second solvent. A preferred first solvent is dimethylsulfoxide.

Granules may be produced by grinding an ester of PGA or PGA-Me-x to a powder with a particle size sufficiently small to be kept in suspension with air, e.g. to a particle size of less than 250 $\mu$m, especially less than 100 $\mu$m, specifically about 10–50 $\mu$m. The powder particles can then be granulated by means of a granulating liquid, typically water comprising sodium alginate in a concentration between 0.1 and 3% w/v, preferably 0.5% w/v, which is sprayed on the suspension. The powder can be mixed with other ingredients commonly used in granulated products, e.g. sodium alginate, polyvinyl pyrrolidone, cellulose derivatives, etc. before being granulated. When the granulation has resulted in a satisfactory particle size, the particles are dried, e.g. by warm air.

An interesting use of the pectic and pectinic acid esters lies in the formulation of micropheres. The microspheres can comprise the esters or salts thereof as the sole ingredient, or they can comprise other ingredients further to one or more of the esters according to the invention or a salt thereof. As the ingredient which is not an ester according to the invention or a salt thereof may be mentioned pharmacologically active substances, selected from the group of substances mentioned above, and especially insulin. The microspheres prepared with the esters according to the invention and, if desired, further ingredients, may be used in the biomedical sector or in the agricultural-alimentary sector.

Microspheres comprising esters according to the invention or salts thereof may be prepared by dissolving the ester or a salt thereof in a solvent, especially an aprotic solvent such as dimethylsulfoxide, at a concentration between 5 and 10% by weight, and adding thereto the other ingredient, such as a pharmacologically active substance, optionally in dissolved form. The liquid phase (discontinuous phase) so prepared can then be emulsified in a continuous phase consisting of e.g. a mineral oil with a surfactant incorporated therein. When the emulsification has been carried out, a liquid in which the ester according to the invention and the optional other ingredient are not soluble, but which liquid is able to extract the solvents of the discontinuous phase, is added under stirring. The amount of liquid phase should preferably be about 2.5 times the total emulsion volume. Once the discontinuous phase solvent has been extracted, the product of the emulsification of the discontinuous phase, the raw microspheres, can be isolated and dried.

If an ester according to the invention is the sole ingredient in the microspheres, a further ingredient such as an active ingredient, e.g. a pharmacologically active ingredient such as insulin can be added to the raw microspheres suspended in a suitable medium. The product formed can then be isolated and dried.

Another use of the esters according to the invention or salts thereof is as additives for food. The esters can be used as thickeners, preservatives, emulsifiers, stabilizers or gelling agents. For example, aliphatic partial esters of PGA or PGA-Me-x in which the aliphatic moiety contains 10–12 carbon atoms, according to the invention, dissolved in water (approximately 1% w/v) can form very stable oil-in-water emulsions (e.g. containing about 20% w/v peanut oil). The same partial esters also exhibit distinct frothing characteristics. For the formation of aqueous gels, partial benzyl esters of PGA can be dissolved (about 1% w/v) in water at 70°–80° C. and a calcium salt can be added (e.g. $CaCl_2$, about 1% w/v).

The mixture is then slowly cooled to allow gel-setting (approximately 24 hours).

When the new esters are formulated into pharmaceutical compositions, these are to be used in a manner corresponding to the actual active ingredient. As an example may be mentioned pharmaceutical compositions in which the pharmacologically active component is a steroidal alcohol which is used as esterifying alcohol. Such a composition is used in a manner corresponding to the known use of the actual steroidal alcohol.

The invention is illustrated by the following examples, without being limited in its scope thereby.

The data relative to PGA concern a sample of PGA, 97% by weight of which is constituted by galacturic acid. Indeed, the equivalent weight of the sample (sodium salt), determined by potentiometer, was 200. A sample with the same characteristics as those described above was obtained from SIGMA Chemical Co. St. Louis, Mo., U.S.A.

The data relative to PGA-Me-x concern a sample of PGA-Me-x with x=35%. The equivalent weight of the sample (sodium salt, containing 80% polygalacturic acid and 20% other neutral sugars) determined by potentiometer was 386. A sample with the same characteristics was obtained from Cesalpina.

The following examples are merely illustrative of methods for obtaining esters of pectic and pectinic acid according to the present invention.

EXAMPLE 1

Preparation of the tetrabutylammonium salts of PGA and PGA-Me-x i) 600 ml, equal to 950 meq of a strongly acid ion exchange resin Dowex 50×8, H+ form, is transformed into tetrabutylammonium (TBA) form by contact under shaking with an aqueous solution of tetrabutylammoniumhydroxide 1.0N.

20 g of PGA (sodium salt) equal to 100 meq are passed through a column containing the resin prepared as specified above.

The eluate is collected, filtered and freeze-dried. 36 g of PGA-TBA are obtained, with a yield of 87%.

ii) An alternative procedure to obtain the PGA-TBA salt is as follows: 20.0 g of a sample of dry PGA (sodium salt), equal to 100.0 meq are solubilized in 1000 ml of distilled water. The solution is passed through a column containing 600 ml of strongly acid ion exchange resin (equal to 950 meq) in acid form.

The eluate is carefully neutralized with tetrabutylammonium hydroxide 1.5M, then filtered and freeze-dried. Yield: 35.7 g (equal to 87% of the theoretical yield)

iii) 30.0 g of sample of PGA-Me-x, with x=35 (sodium salt), equal to 78 meq are solubilized in 1000 ml of distilled water. The solution is passed through a column containing 600 ml of strongly acid ion exchange resin (equal to 950 meq) in acid form.

The eluate is carefully neutralized with tetrabutylammonium hydroxide 1.5M, then filtered and freeze-dried. Yield: 39.0 g (equal to 85% of the theoretical).

EXAMPLE 2

Preparation of the (partial) ester of PGA containing 85% of its carboxyl groups in the form of benzyl ester 35.4 g (84 meq) of the tetrabutylammonium salt of PGA as obtained in Example 1, i) are solubilized in 400 ml of anhydrous dimethylsulfoxide (DMSO) at 25° C. under a current of pure nitrogen.

2 g of 3-tert-butyl-4-hydroxy anisole (free radical inhibitor) are added and pure nitrogen is bubbled through for 12 hours.

17.52 g (102 meq.) of benzyl bromide are added. The solution is shaken well for 2 days at 25° C. and for 1 day at 37° C.

The reaction mixture is poured dropwise into an excess of chilled ethyl acetate (about 0° C.) while shaking, then left to shake for another hour.

The precipitate is filtered and washed with an excess of ethyl acetate, then stirred with a solution of 3% NaCl in ethanol/water 1:1 to convert the unesterified carboxyl groups into the sodium salt.

The precipitate is filtered again and repeatedly washed with ethanol/water 1:1, ethanol and acetone in succession.

The precipitate is then collected and vacuum-dried at 40° C. for 48 hours. 17.0 g of product are thus obtained.

Quantitative determination of the degree of esterification of the PGA derivative was performed by NMR and gas chromatography.

EXAMPLE 3

Preparation of the partial ester of PGA containing 50% of the carboxyl groups in the form of benzyl ester.

10.9 g (26.0 meq.) of the tetrabutylammonium salt of PGA are solubilized in 140 ml of anhydrous DMSO at 25° C. under a current of pure nitrogen.

0.7 g of 3-terbutyl-4-hydroxyanisole are added, maintaining the current of pure nitrogen, and the solution is then shaken for 12 hours.

2.2 g (13 meq.) of benzyl bromide are added. The solution is shaken well for 48 hours at 25° C. and for 24 hours at 37° C.

The reaction mixture is added dropwise to an excess of chilled ethyl acetate (about 0° C.) while stirring and then left to shake for about 1 hour. The precipitate is filtered and washed with an excess of ethyl acetate and stirred with a solution of tetrabutylammonium bromide 1% in water/ethanol 1:1 to ensure that free carboxyl groups are exclusively in the form of the tetrabutylammonium salt and, thereby, to obtain a sample which is easily soluble in DMSO for subsequent NMR analysis. Excess salt is eliminated by prolonged washing with distilled water.

The sample is washed with acetone and then vacuum-dried at 45° C. for 48 hours. Yield: 7 g.

Quantitative determination of the degree of esterification of the PGA derivative was performed by gas chromatography and NMR.

EXAMPLE 4

Preparation of the partial ester of PGA containing 10% of its carboxyl groups in the form of decyl ester.

9.7 g (23.1 meq.) of the tetrabutylammonium salt of PGA are solubilized in 100 ml of anhydrous DMSO at 25° C. under a current of pure nitrogen.

0.5 g of 3-terbutyl-4-hydroxy-anisole are added, still under a current of pure nitrogen for 12 hours.

0.93 g (3.5 meq.) of n-decyl iodide are added. The solution is well shaken for 48 hours at 25° C. and for 24 hours at 37° C.

The reaction mixture is added drop by drop to an excess of chilled acetone (about 0° C.) and left to shake for about one hour.

The precipitate is filtered and washed with an excess of acetone, then stirred with a solution of 3% NaCl in water in order to convert all the unesterified carboxyl groups into sodium salt.

The product, purified by dialysis against distilled water, proves to be easily soluble in water from which it is separated by freeze-drying. Yield: 4.7 g.

Quantitative determination of the degree of esterification of the PGA derivative was performed by gas chromatography.

EXAMPLE 5

Preparation of the mixed ester of PGA containing 50% of its carboxyl groups in the form of benzyl ester and 50% of its carboxyl groups in the form of ethyl ester.

1.0 g (2.4 meq.) of the tetrabutylammonium salt of PGA are solubilized in 30 ml of anhydrous DMSO at 25° C. under a current of pure nitrogen.

0.15 g of 3-terbutyl-4-hydroxy-anisole are added, still under a current of pure nitrogen for 12 hours.

0.3 g (1.8 meq.) of benzyl bromide and 0.28 g (1.8 meq.) of ethyl iodide are added. The solution is well shaken for 48 hours at 25° C. and for 24 hours at 37° C.

The reaction mixture is added dropwise to an excess of chilled acetone (about 0° C.) while shaking, and the mixture is then left to shake for about one hour.

The precipitate is filtered and washed with an excess of acetone, and then vacuum-dried at 45° C. for 48 hours. Yield: 0.5 g.

Quantitative determination of the degree of esterification of the PGA derivative was performed by NMR and gas chromatography.

EXAMPLE 6

Preparation of the benzyl ester (Bz) of PGA-Me-x with x=35 and Bz=65.

1.25 g (2.0 meq.) of the tetrabutylammonium salt of PGA-Me35 are solubilized in 50 ml of anhydrous DMSO at 25° C. under a current of pure nitrogen.

0.25 g of 3-ter-butyl-4-hydroxy-anisole, still under a current of pure nitrogen for 12 hours.

0.7 g (4.0 meq.) of benzyl bromide are added. The solution is well shaken for 48 hours at 25° C. and for 24 hours at 37° C. The reaction mixture is added dropwise to an excess of chilled acetone (about 0° C.) and left to shake for about 1 hour.

The precipitate is filtered and washed with an excess of acetone and then vacuum-dried at 45° C. for 48 hours. Yield: 0.75 g.

Quantitative determination of the benzyl groups present along the chain of the sample was performed by NMR analysis and gas chromatography.

EXAMPLE 7

Frothing characteristics in aqueous medium of the derivative as prepared in Example 4.

30 mg of the product of Example 4 are dissolved in 20 ml of water and the resulting solution is shaken vigorously for 30 seconds in a calibrated 100-ml tube with an airtight cap.

The ratio between the volume of froth measured after 10 seconds and the volume of the liquid phase underneath was 2:5. The froth lasted for many days, albeit with a lesser volume.

The addition of NaCl to the solution makes it cloudy but does not have much influence on the volume of the froth.

EXAMPLE 8

Process for the production of microspheres from partial esters of PGA

A partial ester of PGA, described in example 2, is dissolved in an aprotic solvent such as dimethylsulfoxide, at a concentration varying between 5 and 10% weight/volume, generally 7% w/v. Once the polymer has been solubilized, a polypeptide such as human insulin, at the set concentration, here 5 I.U. per mg of polymer, is added to the solution. The mixture obtained will be referred to hereafter as the discontinuous phase. At the same time, a mixture of highly viscous mineral oil containing arlacel, a non-ionic surfactant, at 1% w/v, is prepared in a reactor.

This mixture will be referred to hereafter as the continuous phase. It is kept at a controlled temperature of 25° C. and stirred at a speed of 1000 RPM while the discontinuous phase described above is added to it.

Emulsification of the two phases is instantaneous in these conditions. The ratio between the two phases (discontinuous and continuous) is about 1:16. After 15 minutes' stirring, ethyl acetate is added. This solvent can be mixed perfectly with the two emulsion phases, but it is not a solvent for the polymer or the human insulin polypeptide. It has been demonstrated that to obtain complete extraction of DMSO, the volume of the extracting solvent should be two and a half times the total volume of the emulsion. To facilitate extraction, the stirring speed should be set at 1,400–1,500 RPM for 10 minutes and then reduced to 500 RPM. The suspension thus obtained is pumped with a screw pump, while still being stirred, into a filter press where the pressure has been set at 1 atmosphere. Once filtration is complete, n-hexane is pumped into the filter, this being a solvent with the double action of drying the preparation and of solubilizing any possible residues of surfactant which may be present on the surface of the microspheres. The product is then collected in suitable containers and stored at 4° C.

In these working conditions, the mean particle size is 15 $\mu$m.

The quantity of incorporated insulin is 4 IU per mg of microspheres.

EXAMPLE 9

Process for the production of microspheres from partial esters of PGA.

A partial ester of PGA, described in Example 2, is dissolved in an aprotic solvent such as dimethylsulfoxide at a concentration varying between 5 and 10% weight/volume, generally 7% w/v. The solution obtained will be referred to hereafter as the discontinuous phase. At the same time, a mixture of highly viscous mineral oil containing arlacel, a non-ionic surfactant, at a concentration of 1% w/v is prepared in a reactor.

This mixture will be referred to hereafter as the continuous phase. This mixture is kept at a temperature of 25° C., stirred at a speed of 1,000 RPM, and to it is added the continuous phase, prepared as previously described.

Emulsification of the two phases is instantaneous in these conditions. The ratio between the two phases (continuous and discontinuous) is about 1 to 16.

After 15 minutes' stirring, ethylacetate is added.

This solvent can be mixed perfectly with the two phases of the emulsion, but it is not a solvent for the polymer. It has been demonstrated that, to obtain complete extraction the volume of the extracting solvent should be two and a half times the total volume of the emulsion. To facilitate extraction, the stirring speed should be set at 1,400–1,500 RPM for 10 minutes, then reduced to 500 RPM. The suspension thus obtained continues to be stirred while it is pumped by a screw pump into a filter press where the pressure has been set at 1 atmosphere. Once filtration is complete, n-hexane is pumped into the filter, this being a solvent with the double action of drying the preparation and solubilizing any possible residues of surfactant which may be present on the surface of the microspheres. The product is then collected in suitable containers and stored at 4° C.

The microspheres thus obtained are suspended in a solution of phosphate buffer containing a concentration of insulin such that a protein titer of 5 I.U. per mg of suspended microspheres is reached. After 15 minutes of stirring by a semiautomatic system, the container is immersed in liquid nitrogen until the suspension is completely frozen.

Once frozen, it is freeze-dried for 24 hours and the freezedried product is then stored at 4° C.

The particle size is 15 microns.

The quantity of incorporated insulin is 5 IU per mg of microspheres.

EXAMPLE 10

Preparation of granules of esters of PGA or PGA-Me-x

The partial ester of PGA, prepared as described in Example 2, is granulated in a fluid bed granulator.

The polymer which is to form the granules is ground to a particle size between 10 and 50 microns. The powder thus obtained is introduced into a reactor and kept in vortex suspension with air, so as to obtain a homogeneous mixture. After 5 minutes a solution of granulating liquid, water containing sodium alginate at a concentration of about 0.5% w/v, is nebulized on the suspension. The polymer particles slowly expand around the droplets which serve as condensation nucleus.

During this last operation the air is heated to 100° C. to allow the water to evaporate from the forming granules and to obtain dry granules as a final product. It is possible to obtain granules with dimensions between 0.5 mm and 1.5 mm, depending on the dimensions of the atomizer and the nebulization pressure.

EXAMPLE 11

Preparation of granules based on bland mixtures of esters of PGA or PGA-Me-x and additives.

The partial ester of PGA, prepared as described in Example 2, is granulated with a fluid bed granulator.

The polymer which is to form the granules is ground to a particle size between 10 and 50 microns. The powder thus obtained is introduced together with excipients commonly used in granulated products, such as sodium alginate, polyvinyl pyrrolidone, cellulose derivatives, etc., into a reactor and kept in vortex suspension with air, so as to obtain a homogeneous mixture. After 5 minutes a solution of granulating liquid, water containing sodium alginate at a concentration of about 0.5% w/v, is nebulized on the suspension. The polymer particles slowly expand around the droplets which serve as condensation nucleus.

During this last operation the air is heated to 100° C. to allow the water to evaporate from the forming granules and to obtain dry granules as a final product. It is possible to obtain granules with dimensions between 0.5 mm and 1.5 mm, depending on the dimensions of the atomizer and the nebulization pressure.

EXAMPLE 12

Emulsifying characteristics in aqueous medium of the derivative described in Example 4.

To 5 ml of an aqueous solution containing 1% in weight of the derivative described in Example 4, are added 0.5 ml of peanut oil.

The mixture is treated with a Vibracell sonicator (Sonics & Materials, USA) and an emulsion is formed by sonicating at minimum power for about 3 minutes.

The emulsion proved to be stable for over 40 days when stored at 4° C.

The following is claimed:

1. Pectic and pectinic acids totally or at least 5% and at the most 95% esterified in which the esterifying component is derived from aliphatic alcohols with a maximum of 34 carbon atoms which are substituted in the aliphatic chain with one or two substituents selected from the group consisting of amino, $C_{1-4}$-hydrocarbylamino, di-($C_{1-4}$ hydrocarbyl)amino, mercapto, aldehydo, keto, carboxyl, $C_{1-4}$-alkoxy and $C_{1-4}$-alkoxycarbonyl, phenyl-$C_{1-4}$-alkyl alcohols, in which the phenyl ring may be substituted by 1–3 substituents selected from the group consisting of methyl, hydroxy and halogen, and wherein the alkyl chain may be substituted by one or two units selected from the group consisting of free amino groups, mono- or diethylated amino groups, pyrrolidine and piperidine groups, aliphatic-cycloaliphatic, cycloaliphatic and heterocyclic alcohols with a maximum of 34 carbon atoms, and salts of such partially esterified pectic and pectinic acids with inorganic or organic bases.

2. Esters of pectic and pectinic acids and salts thereof according to claim 1, wherein the alcohol component is derived from benzyl alcohol, phenethyl alcohol, ephedrine or adrenaline.

3. Esters of pectic and pectinic acids and their salts according to claim 1, wherein the alcohol component derived from cycloaliphatic or aliphatic-cycloaliphatic or heterocyclic alcohols, respectively, is mono- or polycyclic.

4. Esters of pectic and pectinic acids according to claim 1, wherein all the carboxyl groups of pectic and pectinic acids are esterified.

5. Esters of pectic and pectinic acids and their salts according to claim 1, wherein at least 5% and at the most 95% of the carboxyl groups of pectic and pectinic acid are esterified.

6. Esters of pectic and pectinic acids and their salts according to claim 1, wherein the esterifying alcohol component is derived from two different alcohols.

7. Esters of pectic and pectinic acids and their salts according to claim 6, which comprise two different esterifying groups wherein the ratio between the number of said different ester groups varies between 0.1:1 and 1:0.1.

8. Salts of unesterified carboxyl groups in pectic and pectinic acid partially esterified according to claim 1, which salts are derived from alkaline metals, alkaline earth metals, ammonia or organic bases.

9. Salts according to claim 8 which salts are derived from aliphatic, arylaliphatic, cycloaliphatic or heterocyclic amines.

10. A pharmaceutical composition containing as an active ingredient an ester or one of its salts as defined in claim 1 together with an excipient.

11. A pharmaceutical composition according to claim 10, wherein the esterifying alcohol component is derived from a pharmacologically active alcohol.

12. A pharmaceutical composition according to claim 10, wherein the salt of the partial ester is formed with a pharmacologically active compound.

13. A pharmaceutical composition containing a pharmacologically active substance or an association of pharmacologically active substances and a carrier constituted by a total or partial ester of pectic or pectinic acid or by a salt of said partial ester with an inorganic or organic base.

14. A pharmaceutical composition comprising pectic or pectinic acid at least 5% and at the most 95% esterified according to claim 1, salified by an inorganic or organic base, wherein at least a fraction of the carboxyl groups is salified by a therapeutically active base.

15. Cosmetic articles containing an ester of pectic or pectinic acid or one of its salts according to claim 1.

16. Sanitary or surgical articles containing an ester of pectic or pectinic acid or one of its salts according to claim 1.

17. Films or threads comprising esters of pectic or pectinic acid according to claim 1 derived from therapeutically inactive alcohols.

18. Films or threads according to claim 20, wherein said pectic or pectinic acid esters are derived from aliphatic alcohols having a maximum of 12 carbon atons.

19. Microspheres comprising esters of pectic or pectinic acid or salts thereof according to claim 1.

20. Food articles containing one or more esters of pectic or pectinic acid or salts thereof according to claim 1.

* * * * *